United States Patent [19]

Yonemitsu et al.

[11] 4,024,195

[45] May 17, 1977

[54] PROCESS FOR ALKYLATING THE ORTHO-POSITION OF PHENOL COMPOUNDS

[75] Inventors: Eiichi Yonemitsu, Kashiwa; Shizuo Togo; Kenichiro Hashimoto, both of Tokyo; Tomoyuki Yui; Akihiko Sanada, both of Matsudo, all of Japan

[73] Assignee: Mitsubishi Gas Chemical Company, Inc., Tokyo, Japan

[22] Filed: Oct. 15, 1975

[21] Appl. No.: 622,507

[30] Foreign Application Priority Data

Oct. 22, 1974 Japan .............................. 49-121779

[52] U.S. Cl. ..................... 260/621 R; 260/619 R; 260/619 A; 260/620; 260/624 R

[51] Int. Cl.² .................. C07C 39/06; C07C 39/12; C07C 39/17

[58] Field of Search ........... 260/621 R, 619 A, 620, 260/624 R, 624 C, 619 R

[56] References Cited

UNITED STATES PATENTS

| | | |
|---|---|---|
| 2,448,942 | 9/1948 | Winkler et al. ................. 260/621 R |
| 3,446,856 | 5/1969 | Hamilton ....................... 260/621 R |
| 3,707,569 | 12/1972 | van Sorge ...................... 260/621 R |

FOREIGN PATENTS OR APPLICATIONS 717,588  10/1954  United Kingdom ........... 260/621 R

*Primary Examiner*—Bernard Helfin
*Assistant Examiner*—W. B. Lone
*Attorney, Agent, or Firm*—Sherman & Shalloway

[57] ABSTRACT

A process for alkylating the ortho-position of a phenol compound which comprises catalytically reacting a phenol compound containing at least one hydrogen atom at its ortho-position with an alcohol in the gaseous phase, characterized by that the catalyst containing iron oxide, silica, chromium oxide and one or more of alkali metal compound is used.

10 Claims, No Drawings

PROCESS FOR ALKYLATING THE ORTHO-POSITION OF PHENOL COMPOUNDS

FIELD OF THE INVENTION

This invention relates to a process for selectively alkylating the ortho-position of phenol compounds.

More particularly, the invention relates to a process for alkylating the ortho-position of phenol compounds with alcohol at high selectivity and high yield for prolonged periods of time, using a catalyst containing iron oxide, silica, chromium oxide and an alkali metal compound or compounds.

BACKGROUND OF THE INVENTION

Phenol compounds with alkylated ortho-position are useful as various industrial materials. For example, 2,6-xylenol is used as a raw material for polyphenylene ether.

A method has already been known to alkylate the ortho-position of a phenol compound by catalytically reacting the phenol compound with an alcohol in the gaseous phase. In such a method, however, when it is desired to obtain, for example, 2,6-dialkyl phenol, para-substituted products such as a para-alkyl phenol, 2,4-dialkyl phenol and 2,4,6-triaklyl phenol are formed as by-products. These by-products are difficult to separate from the 2,6-dialkyl phenol, and therefore, it is important to inhibit the formation of these by-products as much as possible by raising the selectivity of the reaction.

The conventional processes are all disadvantageous for commerical operation because the selectivity is low or the yield of the object product is low. Furthermore, they have the defect in that the durability of the catalytic activity is low and therefore the catalyst should be exchanged frequently.

For example, U.S. Pat. No. 2,448,942 discloses a process for methylating a phenol compound using a metal oxide, especially aluminum oxide, as a catalyst. However, this process is suitable for obtaining a phenol compound which is substituted with three or more alkyl groups, and the selectivity of the alkylation of ortho-position is low.

British Pat. No. 717,588 discloses a process for preparing 2,6-xylenol by alkylating ortho-cresol with methanol using a metal oxide, preferably aluminum oxide, as the catalyst. However, according to this process, the conversion of ortho-cresol and the selectivity to 2,6-xylenol are very low.

There was another proposal for making 2,6-xylenol by methylating phenol using magnesium oxide as a catalyst. Since this process requires high temperatures, the catalytic activity gradually decreases by the deposition of a carbonaceous substance on the catalyst surface and the growth of the crystallites of magnesium oxide causes an irreversible decrease in its activity, which in turn leads to the necessity of exhanging the catalyst after a short period of time.

It has also been known to use iron oxide as a catalyst, but since it inherently has a low catalytic activity and the activity decrease abruptly, this method has not been utilized commercially. In an attempt to remove these defects of the iron oxide catalyst, method has been proposed in which a mixture of iron oxide and zinc oxide is used as a catalyst (Japanese Patent Publication No. 37812/71). In this method, too, the activity of the catalyst is not sufficient, and especially its durability is unsatisfactory.

We previously proposed as the catalyst for making an ortho-alkylated phenol with high selectivity, two types of catalyst systems, i.e. binary catalyst consisting of iron oxide and silica, and ternary catalyst consisting of iron oxide, silica and chromium oxide (U.S. Pat. Application Ser. No. 476,268). Of those catalysts, the binary catalyst has excellent initial activity, but also has a defect in that the activity gradually decreases as the reaction time is prolonged. Therefore, the catalyst must be regenerated with oxygen-containing gas at a certain time interval. Whereas, the ternary catalyst has a nearly equivalent initial activity and markedly improved durability compared with the binary catalyst. However, the durability being a very important factor of a catalyst from an industrial standpoint, it is extremely desirable to find a catalyst having still more improved durability than that of the ternary catalyst. An object of this invention is to solve that problem.

SUMMARY OF THE INVENTION

This invention provides a process for orthoalkylation of phenol compounds which comprises catalytically reacting a phenol compound containing at least one hydrogen atom at the ortho-position with an alcohol in the gaseous phase to alkylate the ortho-position of the phenol compound, characterized by that the catalyst contains iron oxide, silica, chromium oxide and one or more of alkali metal compounds.

DESCRIPTION OF THE INVENTION

The phenol compound containing at least one hydrogen atom at the ortho-position as used in the present invention is expressed by the following general formula

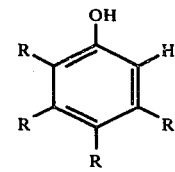

wherein each R independently represents a monovalent substitutent such as hydrogen atom, an alkyl group containing 1 to 6 carbon atoms, aryl group or an alkyl-aryl group.

Specific examples of the phenol compounds include phenol, ortho-cresol, meta-cresol, para-cresol, 2,3-xylenol, 2,4-xylenol, 2,5-xyelnol, 3,5-xylenol, 3,4-xylenol, 2,3,4-trimethylphenol, 2,3,5-trimethylphenol, 2,4,5-trimethylphenol, 2,3,4,5-tetramethylphenol, ortho-ethylphenol, meta-ethylphenol, para-ethylphenol, 2,3-diethylphenol, 2,4-diethylphenol, 2,5-diethylphenol, 3,5-diethylphenol, 3,4-diethylphenol, 2,3,4-triethylphenol, 2,4,5-triethylphenol, orthopropylphenol, ortho-isopropylphenol, ortho-phenylphenol, para-phenylphenol, ortho-cyclohexylphenol and para-cyclohexylphenol.

Examples of the alcohols used in this invention are lower saturated aliphatic alcohols containing 1 to 4 carbon atoms. Ethanol, and especially methanol, are preferred.

The catalyst to be used according to the invention is a quaternary catalyst consisting or iron oxide, silica, chromium oxide and one or more of alkali metal compounds. Examples of the preferred alkali metal compounds are the oxide, carbonate or sulfate of alkali metals (which will be hereinafter expressed as $I_A$) such as lithium, sodium, potassium, rubidium, and cesium. The composition of the quaternary catalyst to be empolyed in this invention, when expressed by atomic ratio, Fe:Si:Cr:$I_A$ is 100:0.1 − 20:0.1 − 5:0.01 −5, preferably 100:0.1−5:0.1−3:0.01−1.0.

For the preparation of the catalyst, first a gel mixture of iron oxide, silica and chromium oxide is formed by the method known per se, such as (a) co-precipitation method, (b) a gel-kneading method, or (c) a method involving kneading gel and a metal salt. Of the named methods, the co-precipitation method is especially preferred. Then the gel-mixture is caused to carry the alkali metal compound or compounds by such a method as (a) impregnation or (b) kneading with the gel, and together calcined. As the means to effect the carrying, particularly the impregnation is preferred.

The method for the preparation of the catalyst of this invention will be described specifically in the following. First mixed aqueous solution containing each predetermined amount of an iron salt, silicon compound and chromium salt is formed, and while stirring the same at 10°–100° C., an alkali agent is added dropwise to the solution, to adjust the pH to 6–8. Stirring is further continued to complete the reaction, and thereby to obtain a precipitate of a hydrogel. The resulting precipitate is thoroughly washed with water, filtered, predried at 100° to 200° C., dipped in an aqueous solution of an alkali metal compound or compounds, filtered, dried at 100° − 200° C., and calcined at 400° − 600° C. for 3 to 15 hours in an air current. Of the catalysts thus obtained, those containing more than 1.5 (by atomic ratio) of silica to 100 of Fe can be imparted with still more increased activity by a pre-treatment with gaseous current of hydrogen at 300° − 450° C. before their use as the catalyst.

Examples of the iron salt to be used in the above method of preparation include ferric nitrate, ferric sulfate, ferric chloride, ferrous nitrate, ferrous sulfate and ferrous chloride. Of these, ferric nitrate is especially preferred.

Examples of suitable silicon compounds are inorganic silicon compounds such as sodium silicate or silica sol (colloidal silica), and organic silicon compounds such as ehtyl orthosilicate.

Examples of suitable chromium compounds are trivalent chromium salts such as chromic nitrate, chromic sulfate or chromic chloride. Chromic acid salts and perchromic acid salts are also used.

Examples of useful alkali metal compounds are nitrates, sulfates, carbonates and hydroxides of lithium, sodium, potassium, rubidium and cesium, particularly the nitrates, sulfates, and carbonates of potassium and lithium being preferred. Presence of a halogen such as a chloride is not recommended.

In the above-described method for the preparation of the catalyst, if a nitrate or hydroxide of alkali metal is used as the alkali metal compound, it is converted to an alkali metal oxide upon calcination. Whereas, if a carbonate or a sulfate of an alkali metal is used, it is substantially free from decomposition during the calcination, and is likely to remain in the catalyst as the carbonate or sulfate.

As the alkali agent to be used in the afore-described catalyst preparation for obtaining the co-precipitated hydrogel of iron oxide, silica and chromium oxide, for example, ammonia, urea, or hydroxide of an alkali metal such as caustic soda can be used, ammonia being the most preferred.

Thus obtained quaternary catalyst according to the invention shows conspicuously improved durability of the catalytic activity compared with the previously proposed ternary catalyst consisting of iron oxide, silica and chromium oxide.

In practicing the ortho-alkylation according to the invention, the suitable molar ratio of the phenol compound and the alcohol to be fed into the reaction zone is 1:1 − 10. Diluent gases which are inert to the reaction, such as steam and nitrogen gas, may be incorporated in the feed gaseous mixture. Especially the incorporation of steam is effective for inhibiting the decomposition of alcohol and consequently, for increasing the recovery ratio of unreacted alcohol, and also for inhibiting the deposition of carbonaceous material on the catalyst surface. The suitable incorporation ratio ranges from 0.5 to 5 mols of steam per mol of the phenol compound.

The reaction temperature employed in the process of this invention is 300° to 450° C., prefereably 310° to 400° C. The reaction pressure may be atmospheric elevated or reduced as the occasion demands. When an elevated pressure is employed, it is suitably from 0.5 to 40 kg/cm$^2$.G.

After the reaction, the resulting reaction product is condensed or caused to be absorbed by an organic solvent, and then separated by, for example, distillation, thereby to afford the desired product.

According to the invention, the reaction can be effected at lower temperatures than those employed in the conventional processes, and hence, undesirable side-reactions can be effectively inhibited. Thus the object ortho-alkylated phenols can be obtained in a high yield not attainable heretofore and at high conversion and selectivity. Furthermore, because the deposition of carbonaceous material on the catalyst surface is little, the catalyst can maintain the high level of activity for a very long period of time.

EXAMPLE 1 AND CONTROL 1

300 grams of ferric nitrate enneahydrate and 2.97 g of chromic nitrate enneahydrate were dissolved in 3 liters of water. Separately, 1.65 g of water glass No. 3 (SiO$_2$ content 30%) was diluted with water and added to the first solution under stirring at room temperature. Then 10% aqueous ammonia was gradually added to the system dropwise, while stirring was continued, until the pH of the liquid reached 7.0. The stirring was further continued for an hour to age the formed hydrogel. The precipitate of the hydrogel was separated by filtration, washed with water and pre-dried for 10 hours at 180° C. The dried gel was pulverized to the size ranging from 6 to 10 mesh, which was dipped in 75 ml of an aqueous solution containing 17.6 mg of potassium carbonate for 16 hours. Thereafter the gel was recovered by filtration, dried for 4 hours at 180° C. and calcined for 470° C. in a stream of air to form the catalyst. The composition of the catalyst thus obtained was, by molar ratio, Fe$_2$O$_3$: SiO$_2$:Cr$_2$O$_3$:K$_2$CO$_3$=100:2:1:0.18.

Forty (40) ml of the catalyst was packed in a stainless steel reaction tube. A gaseous mixture of methanol, phenol and water at a molar ratio of 5:1:1 was passed through the catalyst bed which was maintained at 335°–345° C., at a liquid hourly space velocity (LHSV) of 0.60 kg/l .hr., together with 30 ml/minute of nitrogen gas. The results were as shown in Table 1 below. Also the results of the similar reaction under identical conditions using the ternary catalyst not carrying the alkali metal compound are concurrently given as Control.

Table 1

| | Example 1 $Fe_2O_3$—$SiO_2$—$Cr_2O_3$—$K_2CO_3$ 100: 2: 1: 0.018 (molar ratio) | | | Control 1 $Fe_2O_3$—$SiO_2$—$Cr_2O_3$ 100: 2: 1 (molar ratio) | | |
|---|---|---|---|---|---|---|
| Reaction temp. | 335 – 345° C | | | 335 – 345° C. | | |
| The time after starting of reaction (hrs.) | Conversion of phenol | Yield of 2,6-xylenol | Yield of ortho-cresol | Conversion of phenol | Yield of 2,6-xylenol | Yield of ortho-cresol |
| 4 | 99.9% | 91.3% | 3.76% | 99.94% | 91.5% | 4.6% |
| 100 | 99.8 | 90.7 | 6.90 | 99.85 | 92.9 | 5.05 |
| 200 | 99.8 | 90.7 | 6.90 | 99.44 | 83.51 | 14.13 |
| 300 | 99.7 | 90.6 | 7.00 | 98.8 | 79.04 | 18.27 |
| 400 | 99.75 | 90.1 | 7.16 | | | |
| 500 | 99.7 | 90.0 | 7.30 | | | |

EXAMPLE 2 AND CONTROL 2

The amount of potassium carbonate used in Example 1 was increased to render the composition of the catalyst as follows: $Fe_2O_3$: $SiO_2$: $Cr_2O_3$:$K_2CO_3$=100:2:1:0.20 (molor ratio). Otherwise the catalyst was prepared under the identical conditions with those of Example 1, and used in the similar reaction at 345° – 355° C. The results are shown in Table 2, together with those of Control 2.

Table 2

| | Example 2 $Fe_2O_3$—$SiO_2$—$Cr_2O_3$$K_2CO_3$ 100 : 2 : 1 : 0.20 (molar ratio) | | | Control 2 $Fe_2O_3$—$SiO_2$—$Cr_2O_3$ 100 : 2 : 1 (molar ratio) | | |
|---|---|---|---|---|---|---|
| Reaction temp. | 345 – 355° C. | | | 345 – 355° C. | | |
| The time after starting of reaction (hrs) | Conversion of phenol | Yield of 2,6-xylenol | Yield of ortho-cresol | Conversion of phenol | Yield of 2,6-xylenol | Yield of ortho-cresol |
| 4 | 100% | 93.6% | 1.70% | 99.98% | 92.39% | 1.49% |
| 100 | 100 | 95.06 | 2.40 | 99.92 | 94.0 | 3.36 |
| 200 | 100 | 93.43 | 4.21 | 99.91 | 93.8 | 3.60 |
| 300 | 99.73 | 92.30 | 5.42 | 99.91 | 93.5 | 3.92 |
| 400 | 99.72 | 91.94 | 5.70 | 99.75 | 90.0 | 7.60 |
| 500 | 99.72 | 91.14 | 6.39 | 99.10 | 81.1 | 16.32 |
| 600 | 99.69 | 90.33 | 7.01 | | | |

EXAMPLES 3-5

The catalysts prepared similarly to Example 1 but with various $K_2CO_3$ contents were used and the reactions were conducted at 335° C. The reaction results at the time of 50 hours after starting of the reaction are shown in Table 3. Other reaction conditions were identical with those of Example 1.

EXAMPLES 6-10

The catalysts prepared similarly to Example 1 but $K_2CO_3$ was replaced by other alkali metal compound were used. The reaction results at the time of 50 hours after starting of the reaction are shown in Table 3. Other reaction conditions were identical with those of Example 1.

Table 3

| Example | Catalyst | Reaction temp. | Coversion of phenol | Yield of 2,6-xylenol | Yield of ortho-cresol | Yield of 2,4,6-trimethyl-phenol |
|---|---|---|---|---|---|---|
| 3 | $Fe_2O_3$—$SiO_2$—$Cr_2O_3$—$K_2CO_3$ 100 : 2 : 1 : 0.01 (molar ratio) | 335° C | 99.91% | 91.4% | 6.43% | 1.01% |
| 4 | " 100 : 2 : 1 : 0.04 | 335 | 99.92 | 92.9 | 3.59 | 1.99 |
| 5 | " 100 : 2 : 1 : 0.20 | 335 | 99.98 | 95.3 | 2.42 | 1.33 |
| 6 | $Fe_2O_3$—$SiO_2$—$Cr_2O_3$—$K_2SO_4$ 100 : 2 : 1 : 0.17 | 335 | 99.92 | 91.7 | 6.43 | 0.87 |
| 7 | "—$K_2O$ 100 : 2 : 1 : 0.32 | 335 | 99.90 | 93.7 | 3.38 | 1.62 |
| 8 | "—$Na_2CO_3$ 100 : 2 : 1 : 0.57 | 340 | 99.93 | 92.9 | 4.99 | 1.09 |
| 9 | "—$Rb_2CO_3$ 100 : 2 : 1 : 0.03 | 335 | 99.88 | 91.1 | 6.64 | 1.11 |
| 10 | "—$Li_2CO_3$ 100 : 2 : 1 : 0.03 | 335 | 99.95 | 93.7 | 3.88 | 1.25 |

* The catalyst of Example 7 was that obtained by calcining the $KNO_3$-carrying hydrogel.

EXAMPLES 11-12

Meta-cresol and para-cresol were methylated using the catalyst of Example 5, with the results as shown in Table 4.

Table 4

| | Example 11 | Example 12 |
|---|---|---|
| LHSV Kg/l.hr. | 0.64 | 0.64 |
| Reaction temp. | 340° C. | 335° C. |
| Composition of feed liquid | p-cresol:methanol:$H_2O$=1:5:1 (molar ratio) | m-cresol:methanol:$H_2O$= 1:5:1 (molar ratio) |
| Conversion of p-cresol | 100% | Coversion of m-cresol 100% |
| Yield of 2,4,6-trimethyl-phenol | 95.2% | Yield of 2,3,6-trimethyl-phenol 94.1% |
| Yield of 2,4- | 0.70% | 2,3- 0.08% |

Table 4-continued

|  | Example 11 | Example 12 |  |
|---|---|---|---|
| Yield of tetramethylphenols | xylenol 1.2% | xylenol Yield of 2,5-xylenol | 0.40% |

EXAMPLE 13

Ortho-isopropylphenol was methylated using the catalyst of Example 5, with the results as shown in Table 5.

Table 5

| Reaction temp. | 340° C |
|---|---|
| LHSV | 0.42 Kg/l.hr. |
| Composition of liquid feed | ortho-isopropylphenol:methanol: $H_2O$=1:3:0.5 (molar ratio) |
| Conversion of ortho-isopropylphenol | 98.6% |
| Yield of ortho-cresol | 2.80% |
| Yield of 2,6-xylenol | 16.12% |
| Yield of 2-methyl-6-isopropylphenol | 75.22% |

EXAMPLE 14

A catalyst having the composition of $Fe_2O_3$: $SiO_2$:$Cr_2O_3$:$K_2CO_3$=100:5:1:0.17(molar ratio) was subjected to a pre-treatment with hydrogen gas passed at a space velocity of 600 hr$^{-1}$ at 350° C. for 8 hours. Then the catalyst was used in the reaction under the identical conditions with those of Example 1 except that the reaction temperature was 345° C. The results obtained at the time of four hours after starting of the reaction were as given in Table 6 below:

Table 6

| Reaction temp. | 345° C. |
|---|---|
| Conversion of phenol | 99.8% |
| Yield of 2,6-xylenol | 91.7% |
| Yield of o-cresol | 5.32% |
| Yield of 2,4,6-trimethylphenol | 1.56% |

What we claim is:

1. In a process of alkylating the ortho-position of a phenol compound by catalytically reacting a phenol compound expressed by the general formula

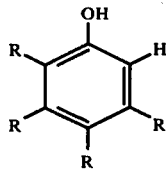

wherein each R independently represents a monovalent substituent selected from the group consisting of a hydrogen atom, alkyl containing 1 to 6 carbon atoms, phenyl and cyclohexyl, with a lower saturated aliphatic alcohol containing 1 to 4 carbon atoms in the gaseous phase at a temperature of 300° to 450° C. in the presence of a catalyst which is a mixture of iron oxide, silica and chromium oxide in which the atomic ratio of iron to silicon to chromium is within the range of 100:0.1–20:0.1–5, the improvement comprising further incorporating in said catalyst mixture at least one alkali metal compound in an amount sufficient to provide an atomic ratio of iron to silicon to chromium to alkali metal in the catalyst within the range of 100:01–20:0.1–5:0.01–5.

2. The process of claim 1 in which the atomic ratio is 100:0.1 – 5:0.1 – 3:0.01 – 1.

3. The process of claim 1 in which the molar ratio of the phenol compound to the alcohol is 1:1 – 10.

4. The process of claim 1 in which the contact of the phenol compound with the alcohol in the gaseous phase is effected in the presence of a diluent gas which is inert to the reaction.

5. The process of claim 4 in which the diluent gas is steam, and is used in the amount of 0.5 to 5 mols per mol of the phenol compound.

6. The process of claim 1 wherein said alkali metal compound is selected from the group consisting of alkali metal oxide, alkali metal carbonate and alkali metal sulfate or mixtures thereof, said alkali metal being selected from the group consisting of lithium, sodium, potassium, rubidium and cesium.

7. The process of claim 1 wherein said alkali metal compound is selected from the group consisting of potassium carbonate, potassium sulfate, potassium oxide, sodium carbonate, rubidium carbonate and lithium carbonate.

8. The process of claim 1 wherein said alkali metal compound is potassium carbonate.

9. The process of claim 1 wherein said phenol compound is phenol and said catalyst is a mixture of iron oxide, silica, chromium oxide and potassium carbonate in a molar ratio of 100:2:1:0.01–0.20.

10. The process of claim 1 wherein said phenol compound is a member selected from the group consisting of phenol, orthocresol, meta-cresol, para-cresol, 2,3-xylenol, 2,4-xylenol, 2,5-xylenol, 3,5-xylenol, 3,4-xylenol, 2,3,4-trimethylphenol, 2,3,5-trimethylphenol, 2,4,5-trimethylphenol, 2,3,4,5-tetramethylphenol, ortho-ethylpehnol, meta-ethylphenol, para-ethylphenol, 2,3-diethylphenol, 2,4-diethylphenol, 2,5-diethylphenol, 3,5-diethylphenol, 3,4-diethylphenol, 2,3,4-triethylphenol, 2,4,5-triethylphenol, ortho-propylphenol, ortho-isopropylphenol, ortho-phenylphenol, para-phenylphenol, ortho-cyclohexylphenol and para-cyclohexylphenol.

* * * * *